United States Patent [19]
Burke

[11] Patent Number: 5,931,859
[45] Date of Patent: Aug. 3, 1999

[54] FACIAL TONING SYSTEM

[76] Inventor: Robert E. Burke, 424 22nd St., Belleair Beach, Fla. 33786

[21] Appl. No.: 09/163,777

[22] Filed: Sep. 30, 1998

[51] Int. Cl.⁶ .................................................... A61N 1/08
[52] U.S. Cl. .............................. 607/66; 604/20; 132/317
[58] Field of Search .................................. 132/314, 317, 132/333; 607/75, 76, 66, 150, 151, 153; 604/20

[56] References Cited

U.S. PATENT DOCUMENTS

| | | | |
|---|---|---|---|
| 1,585,104 | 5/1926 | Montgomery | 604/20 |
| 3,107,672 | 10/1963 | Hofmann | 607/151 |
| 5,443,441 | 8/1995 | De Claviere | 604/20 |
| 5,514,167 | 5/1996 | Smith et al. | 607/151 |
| 5,618,275 | 4/1997 | Bock | 604/20 |

*Primary Examiner*—Todd E. Manahan
*Assistant Examiner*—Eduardo C. Robert
*Attorney, Agent, or Firm*—Ronald E. Smith

[57] ABSTRACT

A three phase facial toning system includes an applicator having an applicator electrode and a ground electrode that are electrically separated from one another by an insulated base. When the applicator is used, the user's hand is in contact with the ground electrode so that the ground electrode is grounded when in use. In the first phase, a cleanser is applied to facial skin, a first switch actuator is pressed, and the applicator electrode is placed into contact with the skin in a prescribed way. Pressing the first switch actuator places the applicator electrode in communication with a positive voltage so that electrons flow from the user's skin to the applicator electrode to help the cleansing action of the cleanser. In the second phase, a vitalizing gel is applied to the face and a second switch actuator is actuated. A voltage oscillates between the applicator electrode and the ground electrode at a predetermined rate of oscillation so that electrons alternately flow into and out of the user's skin to assist the action of the vitalizer. In the third phase, a moisturizer is applied to the skin and a third switch actuator is actuated. Electrons then flow from the applicator electrode into the skin to enhance the effectiveness of the moisturizer. A housing includes three wells for holding jars that contain the cleanser, vitalizer, and moisturizer and a fourth well that holds the applicator and a power cord that extends from the applicator to the circuit that controls the current flow to the electrodes. Batteries supply power to the circuit.

9 Claims, 5 Drawing Sheets

FACIAL TONING SYSTEM

BACKGROUND OF THE INVENTION

1. Field of the Invention

This invention relates, generally, to an electromechanical device having utility in the art of facial care. More particularly, it relates a system that electronically applies creams and gels to the face and neck in three distinct phases.

2. Description of the Prior Art

Facial toning systems heretofore known require a service provider to hold an applicator having an electrode at a first electrical potential and require a(customer to hold a ground electrode so that current flows from the applicator into the customer's skin when the service provider applies the applicator to the skin of the customer's face and neck. The difference in potential helps facial cream pre-applied to the customer's face and neck to enter into the customer's skin. More specifically, electrons flow from the applicator into the skin and said flow helps to carry the creams into the skin.

These well-known systems have several limitations. First, many customers don't care to hold an electrode in their hands during treatment. Second, the difference in potential is always in one direction; thus, creams or gels may be driven into the skin, but reverse current flow that could help retract unwanted chemicals or skin particles out of the skin is not available. Moreover, an oscillating current of the type that could help revitalize skin is not available. Finally, and perhaps most importantly, such systems cannot be self-administered because they require two people, i.e., one for each electrode.

A system operable by a single person is therefore needed. The needed system would eliminate the need for a second electrode held by a customer and would also provide current flow in more than one direction to assist in applying and removing wanted and unwanted substances, respectively. Moreover, an improved system would also provide an oscillating current flow to firm and tone the skin.

However, in view of the art considered as a whole at the time the present invention was made, it was not obvious to those of ordinary skill in this art how the needed improvements could be provided.

SUMMARY OF THE INVENTION

The long-standing but heretofore unfulfilled need for an apparatus that overcomes the limitations of the prior art is now met by a new, useful, and nonobvious invention. The present invention includes an applicator having an insulated base, an applicator electrode extending from a first end of the insulated base and a ground electrode extending from a second end of the insulated base. A source of electrical power is in independent electrical communication with the applicator electrode and the ground electrode. A first, second and third switch means, actuated by associated push buttons, are disposed in circuit-opening and circuit-closing relation between the source of electrical power and the applicator. The novel apparatus further includes a circuit means, including said first, second and third switch means, that applies a predetermined positive voltage to the applicator electrode when the first switch means is closed, that applies a predetermined voltage that oscillates between the applicator electrode and the ground electrode when the second switch means is closed, and that applies a positive voltage to the ground electrode when the third switch means is closed. The ground electrode is adapted to be held by a user's hand so that the circuit is grounded. The circuit, when the first switch means is closed, opens the second and third switch means. When the applicator electrode is then held against the user's skin while the ground applicator is held in the user's hand, electrons flow from the user's skin to the applicator electrode. Closing the second switch means opens the first and third switch means. When the applicator electrode is then held against the user's skin while the ground applicator is held by the user, electrons flow at a predetermined oscillation rate from the applicator electrode:into the user's skin and from the user's skin into the applicator electrode. Closing the third switch means opens the first and second switch means. When the applicator electrode is then held against the user's skin while the ground electrode is held by the user, electrons flow from the applicator electrode into the user's skin. In this way, the user's skin is defoliated when the first switch means is closed, is firmed and toned when the second switch means is closed, and is cleansed when the third switch means is closed.

It is a primary object of this invention to advance the art of facial toning systems by providing a system that can be used by an individual without assistance from a second individual.

Another object is to provide a facial toning system that includes electronic means for applying and withdrawing substances into and from the skin, respectively.

Still another object is to provide a facial toning system that provides facial toning and firming.

These and other important objects, features, and advantages of the invention will become apparent as this description proceeds.

The invention accordingly comprises the features of construction, combination of elements and arrangement of parts that will be exemplified in the construction hereinafter set forth, and the scope of the invention will be indicated in the claims.

BRIEF DESCRIPTION OF THE DRAWINGS

For a fuller understanding of the nature and objects of the invention, reference should be made to the following detailed description, taken in connection with the accompanying drawings, in which.

DETAILED DESCRIPTION OF THE PREFERRED EMBODIMENT

Figure 1:
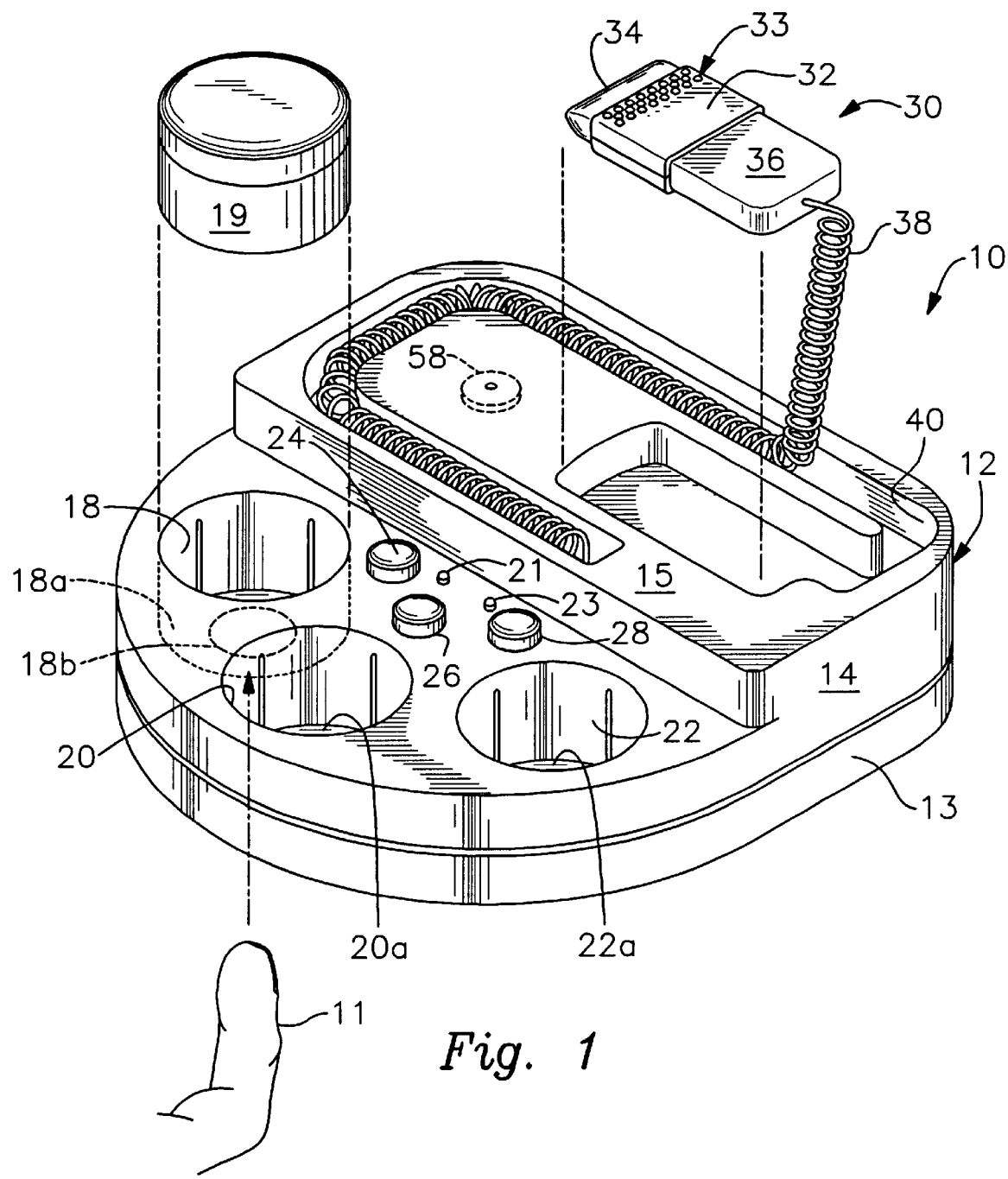
FIG. 1 is an exploded perspective view of the novel apparatus.

Referring now to FIG. 1, it will there be seen that an exemplary embodiment of the invention is denoted as a whole by the reference numeral 10.

Novel facial toning system 10 includes a housing 12 that includes bottom piece 13 and base 14. Three wells 18, 20 and 22 are formed in base 14 for removably receiving a jar of exfoliation cream 19, a jar of vitalizing gel, not shown to avoid cluttering the drawing, and a jar of moisturizing cream, also not shown, respectively. Each well has a bottom wall 18a, 20a, 22a having a central aperture 18b, 20b and 22b (see also FIG. 3) formed therein, respectively, as depicted to facilitate removal of each jar from its well by protruding a finger 11 (FIG. 1) through such aperture.

Push buttons or switch actuators 24, 26 and 28 (FIG. 1) actuate first, second and third switch means 24a, 26a and 28a (FIG. 5A), respectively. Said push buttons are mounted in base 14 adjacent their associated wells 18, 20 and 22, respectively, as are green indicator lamps 21 and 23. This positioning of said buttons is advantageous because the user will intuitively know which button to press when using a particular jar. The buttons and wells are also marked I, II and III.

Applicator 30 includes plastic base 32, applicator electrode 34 and ground electrode 36. Elongate coiled power cord 38 extends from the ground electrode end of applicator 30 to a source of direct current mounted below base 14.

Figure 2:
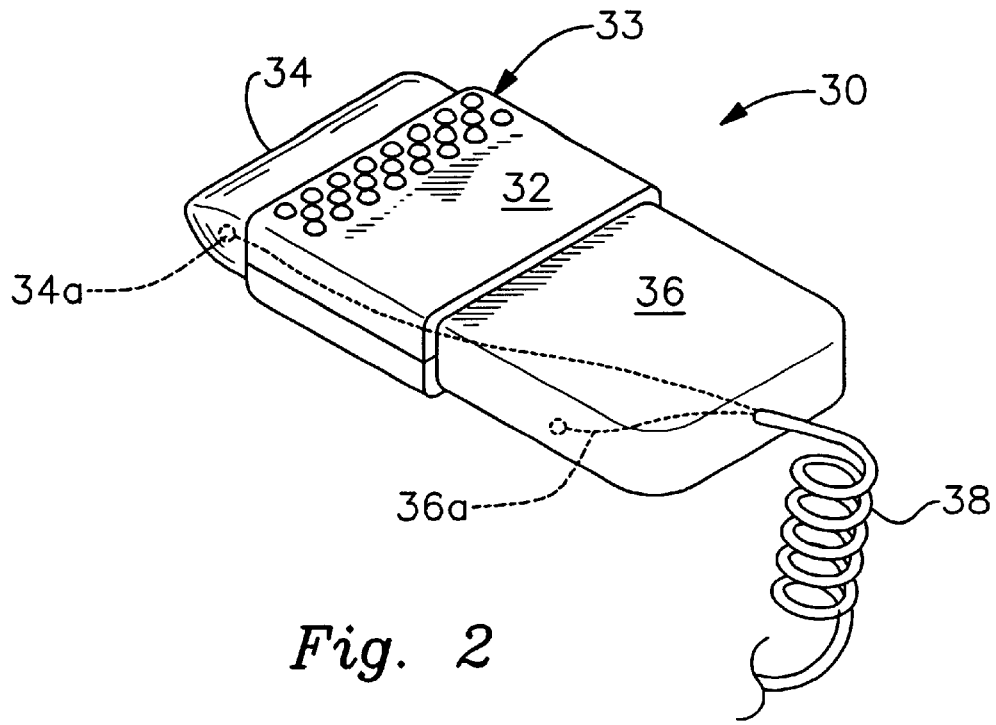
FIG. 2 is a perspective view of the novel applicator.

Note from FIG. 2 that conductor 34a is electrically connected to applicator electrode 34 and that conductor 36a is electrically connected to ground electrode 36. Base 32 is formed of an insulating material and there is no electrical circuit between electrodes 34, 36 unless a user touches both of said electrodes simultaneously.

The positioning of power cord 38 is advantageous because a user will know intuitively that the opposite end 34 of applicator 30 is the end that will contact the face and neck. Thus, the user will know to grip ground electrode 36 and not applicator electrode 34; the latter is also too short to grip.

Figure 3:
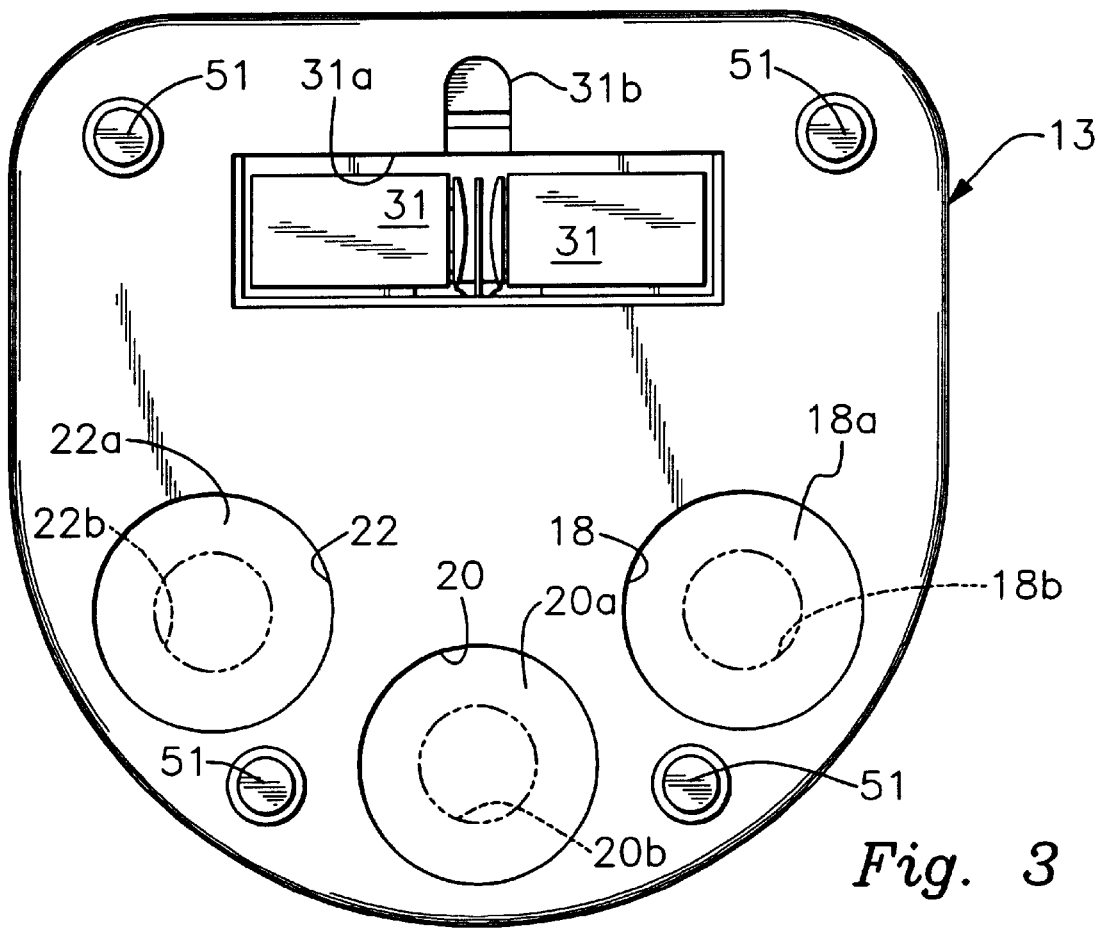
FIG. 3 is a bottom plan view of the novel apparatus.

As indicated in FIG. 3, the preferred power source is a pair of nine volt batteries, collectively denoted 31; the potential difference between applicator electrode 34 and ground electrode 36 is therefore eighteen volts. Batteries 31 are positioned within a battery well 31a formed within bottom piece 13. A cover including slideable handle 31b encloses batteries 31 within battery well 31a in a well-known way.

Applicator 30 and power cord 38 are stored in elongate, serpentine well means 40 formed in a raised section of base 14. They are flush with a top surface 15 of said raised section when stored in said well 40 and are covered with a lid means, not shown, that mates with said raised section.

The electronic circuit board that controls operation of the novel system is mounted below base 14 and is denoted 50 in FIG. 4; the schematic diagram of the circuitry mounted thereon is also denoted 50 in FIGS. 5A and 5B.

A complete facial treatment begins with the application of a small amount of cleansing cream to the face, including the neck if desired. The cream is not manually massaged into the skin. Any cleansing cream that may be left on the hand is removed with a suitable cloth before applicator 30 is picked up. Button 24 is pressed and green indicator lamp 21 illuminates momentarily to indicate that batteries 31 are functioning properly. Green indicator lamp 23 illuminates when ground electrode 36 has been gripped by the user and when applicator electrode 34 has touched the user's skin. A piezo buzzer 58 (FIG. 5A) sounds momentarily after the elapse of a predetermined amount of time, such as four or five minutes or so, to advise the user that the first phase of the treatment has ended and that it is time to apply a small quantity of the contents of the jar associated with well 20 to the areas to be treated.

Applicator 30 is hand-held, with the fingers gripping ground electrode 36. The fingers may also rest atop insulated plastic base 32, as long as the fingers also touch said ground electrode 36. A few rows of dimples 33 (FIGS. 1 and 2) are formed in the leading edge of plastic base 32 to remind the user to maintain the fingers away from applicator electrode 34. Pressing button 24 actuates first switch means 24a and applies a positive voltage to applicator electrode 34 and a negative voltage to ground electrode 36. This causes electrons to flow out of the user's skin, thereby assisting the action of the cleanser and defoliating the skin and providing a deep cleaning.

A vitalizing gel is then applied to the cleaned skin from the jar of well 20 and button 26 is pressed to actuate second switch means 26a. Lamp 21 illuminates momentarily if the batteries are functioning properly, and lamp 23 flashes when the circuit is completed in the manner described above. Buzzer 58 sounds momentarily after about seven or eight minutes, advising the user that the second phase has been completed. During the second phase, circuit 50 produces a square wave eighteen volt alternating current across applicator and ground electrodes 34 and 36, respectively, oscillating at a frequency of about ten to twenty Hertz. Thus, electrons are removed from and reinjected into the skin at that frequency; when coupled with the vitalizing gel, the face is firmed and toned.

A moisturizer cream from the jar associated with well 22 is then applied and third button 28 is pressed, actuating third switch means 28a. Lamp 21 illuminates if the batteries are OK, lamp 23 illuminates when the circuit is completed by touching applicator electrode 34 to the face while holding ground electrode 36. A negative voltage is applied to applicator electrode 34 and a positive voltage is applied to ground electrode 36. This causes electrons to flow into the face, carrying the moisturizer with them, and thus delivering moisturizer to the cleaned, firmed and toned skin. After the passage of a predetermined amount of time, such as four minutes, buzzer 58 sounds momentarily to advise the user that one session of the treatment has been concluded.

Instructions concerning how frequently to repeat the sessions are provided in literature that will accompany the commercial embodiment of this invention, together with detailed instructions concerning what quantities of each cream or gel to apply, how to apply them, and so on.

Figure 4:
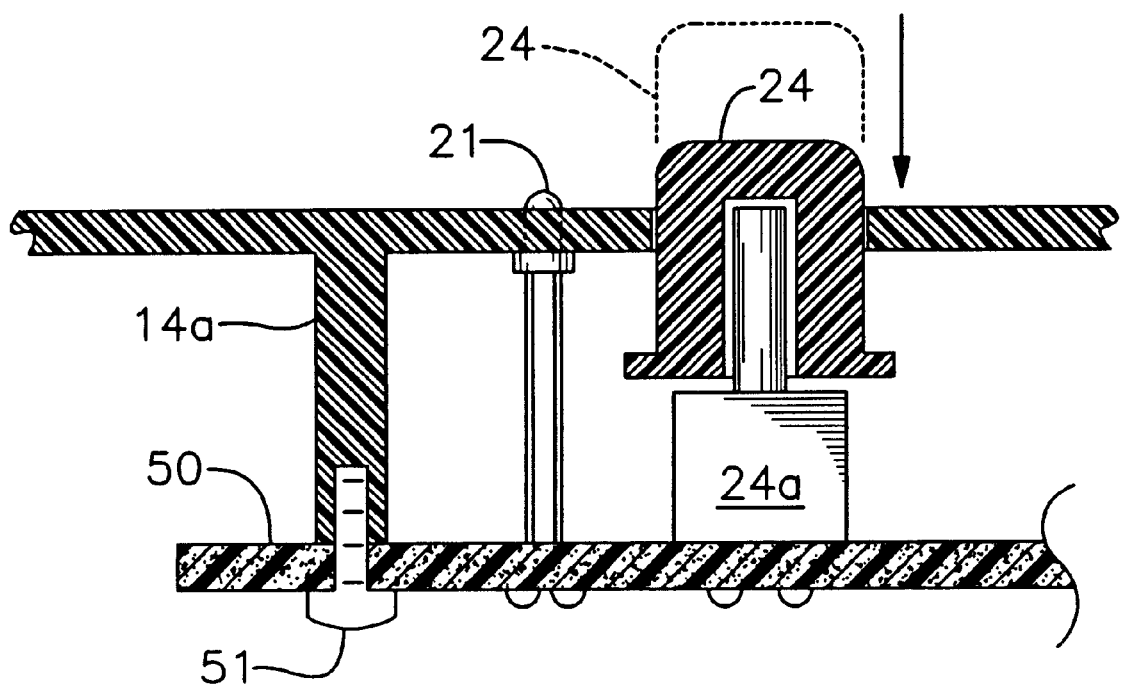
FIG. 4 is a sectional view of the base of the novel apparatus, depicting the mounting of the buttons, indicator lamps, and circuit board.

A few construction details are depicted in FIG. 4. There it will be seen that screws 51 (also depicted in FIG. 3) secure circuit board 50 to stand-offs 14a which are formed integrally with base 14 and which depend therefrom. Indicator lamps 21, 23 and buttons 24, 26 and 28 extend through openings formed in base 14 and said lamps and the respective switch means associated with the push buttons are electrically connected at their respective lowermost ends to circuit board 50. Stand-offs 14a serve further as alignment means to assist in proper positioning of circuit board 50 during assembly of novel device 10.

Figure 5A:
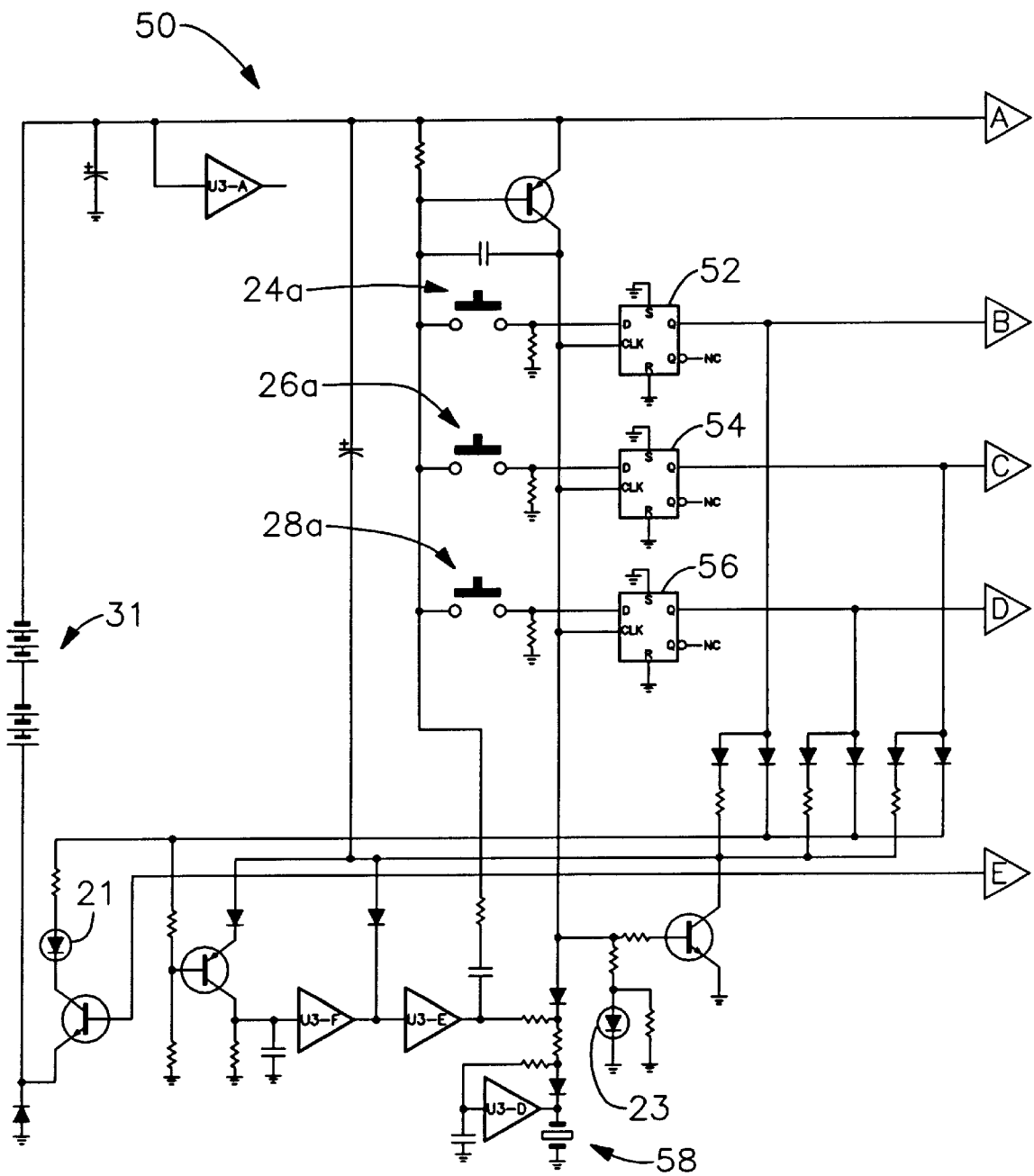
FIG. 5A is a schematic diagram of a first part of the electronic circuit that controls the application of voltage to the applicator.
Figure 5B:
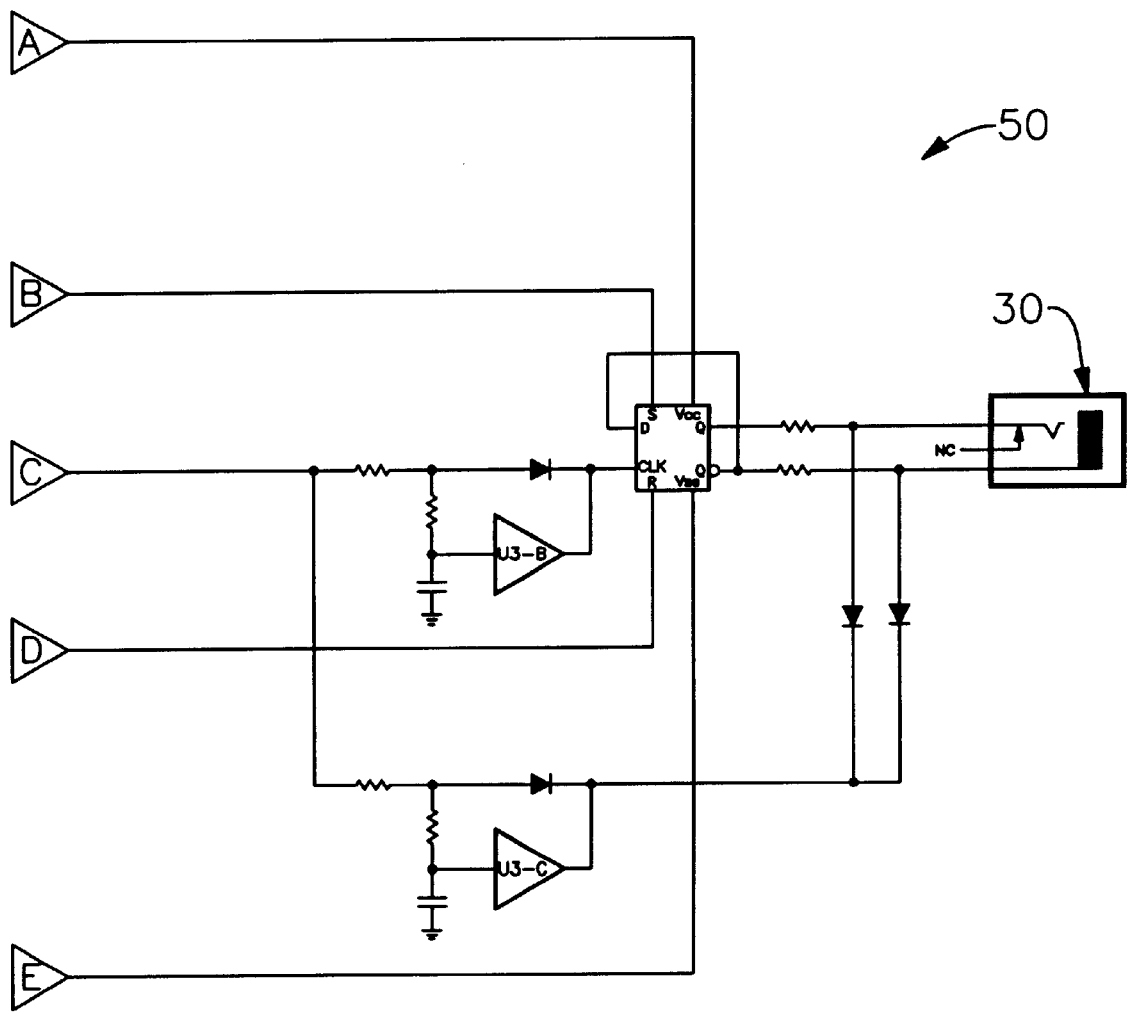
FIG. 5B is a schematic diagram of a second part of said electronic circuit.

As indicated in FIGS. 5A and 5B, novel circuit 50 includes flip flops (bistable multivibrators) 52, 54 and 56 in electrical communication with switch means 24a, 26a and 28a, respectively, so that actuation of one switch means deactuates the other switch means.

It will thus be seen that the objects set forth above, and those made apparent from the foregoing description, are efficiently attained and since certain changes may be made in the foregoing construction without departing from the scope of the invention, it is intended that all matters contained in the foregoing construction or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described,
What is claimed is:

1. A facial toning system, comprising:

an applicator having an insulated base, an applicator electrode extending from a first end of said insulated base, and a ground electrode extending from a second end of said insulated base;

a source of electrical power in electrical communication with said applicator electrode and said ground electrode;

a first, second and third switch means disposed in circuit-opening and circuit-closing relation between said source of electrical power and said applicator;

a circuit means, including said first, second and third switch means, for applying a predetermined positive voltage to said applicator electrode when said first switch means is closed and when said applicator is held by a user at said ground electrode and said applicator electrode is in contacting relation to the user's skin, for applying a predetermined voltage that oscillates between said applicator electrode and said ground electrode when said second switch means is closed and when said applicator is held by said user at said ground electrode and said applicator electrode is in contacting relation to said user's skin, and for applying a positive voltage to said ground electrode when said third switch means is closed and when said applicator is held by said user at said ground electrode and said applicator electrode is in contacting relation to said user's skin;

said applicator electrode and said ground electrode being electrically insulated from one another so that a circuit is completed when a predetermined switch means is closed and when said applicator electrode is grounded by being held in said user's hand and said applicator electrode is held by said user in contacting relation to said user's skin;

said circuit, when said first switch means is closed, when said second and third switch means are open and when said applicator electrode is held against said user's skin by said user while said ground applicator is held in said user's hand, causing electrons to flow from said user's skin to said applicator electrode;

said circuit, when said second switch means is closed, when said first and third switch means are open and when said applicator electrode is held against said user's skin by said user while said ground applicator is held in said user's hand, causing electrons to alternately flow, at a predetermined oscillation rate, from said applicator electrode into said user's skin and from said user's skin into said applicator electrode;

said circuit, when said third switch means is closed, when said first and second switch means are open and when said applicator electrode is held against said user's skin by said user while said ground applicator is held in said user's hand, causing electrons to flow from said applicator electrode into said user's skin;

whereby the user's skin is defoliated when said first switch is closed;

whereby said skin is firmed and toned when said second switch is closed; and whereby said skin is cleansed when said third switch is closed.

2. The facial toning system of claim 1, further comprising:

an elongate power cord interconnecting said applicator and said source of electrical power;

said elongate power cord including a first electrical conductor connected to said applicator electrode and a second electrical conductor connected to said ground electrode.

3. The facial toning system of claim 2, further comprising:

a base member;

a plurality of wells formed in said base member;

a predetermined number of said wells adapted to releasable hold a jar; and one of said wells adapted to releasable hold said applicator and said elongate power cord.

4. The facial toning system of claim 3, wherein said predetermined number of wells adapted to releasable hold a jar is three, wherein a first well is adapted to hold a jar of cleanser, wherein a second well is adapted to hold a jar of vitalizer, and wherein a third well is adapted to hold a moisturizer.

5. The facial toning system of claim 4, further comprising a first switch actuator means mounted in said base member adjacent said first well, said first switch actuator means actuating said first switch means, a second switch actuator means mounted in said base member adjacent said second well, said second switch actuator means for actuating said second switch means, and a third switch actuator means mounted in said base member adjacent said third well, said third switch actuator means for actuating said third switch means, so that a user of said system will intuitively know which switch actuator to actuate when beginning a phase of treatment involving said cleanser, said vitalizer, or said moisturizer.

6. The system of claim 1, wherein said circuit includes a bistable multivibrators in electrical communication with each of said switch means so that each of said switch means toggles from its closed configuration to its open configuration or from its open configuration to its closed configuration each time it is actuated.

7. The system of claim 1, further comprising a first lamp means in electrical connection with said power source and in electrical connection with each of said switch means so that said first lamp illuminates momentarily when a switch means is closed and if said power source is functioning.

8. The system of claim 1, further comprising a second lamp means in electrical connection with said power source, said second lamp means being illuminated when said ground electrode is held by a user's hand and when said applicator electrode is in contacting relation to the skin of the user.

9. The system of claim 1, further comprising a buzzer means that sounds momentarily a predetermined amount of time after a predetermined switch means is closed to audibly advise a user that a phase of the treatment has ended.

* * * * *